United States Patent
Eguchi et al.

(10) Patent No.: US 10,744,134 B2
(45) Date of Patent: Aug. 18, 2020

(54) PHARMACEUTICAL COMPOSITION FOR CANCER IMMUNOTHERAPY AND/OR IMMUNOLOGICAL ACTIVATION CONTAINING DIAMINO HETEROCYCLIC CARBOXAMIDE COMPOUND AS ACTIVE INGREDIENT

(71) Applicant: Astellas Pharma Inc., Chuo-ku (JP)

(72) Inventors: Tomohiro Eguchi, Tokyo (JP); Taku Yoshida, Tokyo (JP); Ruriko Kado, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 209 days.

(21) Appl. No.: 15/773,225

(22) PCT Filed: Nov. 2, 2016

(86) PCT No.: PCT/JP2016/082536
§ 371 (c)(1),
(2) Date: May 3, 2018

(87) PCT Pub. No.: WO2017/078049
PCT Pub. Date: May 11, 2017

(65) Prior Publication Data
US 2018/0318295 A1 Nov. 8, 2018

(30) Foreign Application Priority Data
Nov. 4, 2015 (JP) .................. 2015-217152

(51) Int. Cl.
| | |
|---|---|
| A61K 38/00 | (2006.01) |
| A61K 31/497 | (2006.01) |
| A61K 31/496 | (2006.01) |
| A61K 39/395 | (2006.01) |
| A61P 35/00 | (2006.01) |
| A61K 39/00 | (2006.01) |

(52) U.S. Cl.
CPC .......... *A61K 31/497* (2013.01); *A61K 31/496* (2013.01); *A61K 39/395* (2013.01); *A61K 39/3955* (2013.01); *A61P 35/00* (2018.01); *A61K 2039/505* (2013.01)

(58) Field of Classification Search
CPC .................................................. A61K 31/497
See application file for complete search history.

(56) References Cited

U.S. PATENT DOCUMENTS

| | | |
|---|---|---|
| 2012/0040968 A1 | 2/2012 | Shimada et al. |
| 2015/0118222 A1 | 4/2015 | Levy et al. |
| 2016/0168121 A1 | 6/2016 | Inukai et al. |
| 2016/0185870 A1 | 6/2016 | Van Eenennaam et al. |
| 2016/0339020 A1 | 11/2016 | Eguchi et al. |

FOREIGN PATENT DOCUMENTS

| | | |
|---|---|---|
| EP | 2 428 508 A1 | 3/2012 |
| EP | 3 103 453 A1 | 12/2016 |
| WO | WO 2010/008411 A1 | 1/2010 |
| WO | WO 2010/128659 A1 | 11/2010 |
| WO | WO 2015/012298 A1 | 1/2015 |
| WO | WO 2015/016718 A1 | 2/2015 |
| WO | WO 2015/054642 A2 | 4/2015 |
| WO | WO 2015/061752 A1 | 4/2015 |
| WO | WO 2015/119122 A1 | 8/2015 |

OTHER PUBLICATIONS

Extended European Search Report dated May 15, 2019 in Patent Application No. 16862109.2, 8 pages.
Myers, S. H. et al., "AXL Inhibitors in Cancer: A Medicinal Chemistry Perspective", Journal of Medicinal Chemistry, XP009500027, vol. 59, No. 8, Nov. 10, 2015, pp. 3593-3608.
M. Jane Ehrke, "Immunomodulation in cancer therapeutics," International Immunopharmacology, vol. 3, 2003, 8 Pages.
Toshio Yoshizawa, et al., "Abstract LB-218: Development of Axl/Mer inhibitor, ONO-9330547: preclinical evidence supporting the combination with immunotherapeutics," Proceedings of the 107th Annual Meeting of the American Association for Cancer Research, Apr. 2016, 2 Pages.
Kohei Tanaka, et al., "Abstract LB-259: The potent and selective Axl/Mer dual inhibitor ONO-9330547, shows promising single agent activity in non-small cell lung cancer (NSCLC)," Proceedings of the 106th Annual Meeting of the American Association for Cancer Research, Apr. 2015, 2 Pages.
Parisa Momtaz, et al., "Immunologic checkpoints in cancer therapy: focus on the programmed death-I (PD-I) receptor pathway," Pharmacogenomics and Personalized Medicine, vol. 7, 2014, pp. 357-365.
Jose Luis Perez-Gracia, et al., "Orchestrating immune check-point blockade for cancer immunotherapy in combinations," Current Opinion in Immunology, vol. 27, 2014, pp. 89-97.

*Primary Examiner* — Sheela J. Huff
(74) *Attorney, Agent, or Firm* — Oblon, McClelland, Maier & Neustadt, L.L.P.

(57) ABSTRACT

6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof has an excellent immunological activation effect, and a pharmaceutical composition containing the compound or the pharmaceutically acceptable salt thereof as an active ingredient is expected to be used as a pharmaceutical composition for cancer immunotherapy and/or as a pharmaceutical composition for immunological activation.

4 Claims, 3 Drawing Sheets

PHARMACEUTICAL COMPOSITION FOR CANCER IMMUNOTHERAPY AND/OR IMMUNOLOGICAL ACTIVATION CONTAINING DIAMINO HETEROCYCLIC CARBOXAMIDE COMPOUND AS ACTIVE INGREDIENT

TECHNICAL FIELD

The present invention relates to a pharmaceutical composition for cancer immunotherapy and/or immunological activation containing diamino heterocyclic carboxamide compound or a pharmaceutically acceptable salt thereof as an active ingredient.

BACKGROUND ART

The immune system excludes cancer by immunosurveillance in the early stage of cancer development and by anti-tumor immunity after cancer manifestation. On the other hand, the cancer in a cancer microenvironment acquires an immune escape mechanism by affecting an immune checkpoint mechanism such as PD-1 (programmed cell death-1)/PD-L1 (programmed cell death-1 ligand-1) or PD-L2 route, or CTLA-4 (cytotoxic T-lymphocyte associated antigen 4)/CD80 or CD86 route and directly suppressing activated T cells, or by indirectly suppressing the activated T cells through induction of regulatory T cells or bone marrow-derived regulatory cells and production of an immunosuppressive humoral factor (IL-10, TGF-β, indoleamine 2,3-dioxygenase (IDO), or the like). The cancer immunotherapeutic agent using an immunomodulator that suppresses these immune escape mechanisms has been vigorously under clinical development for use as a promising therapeutic agent alone or in combination with other immunomodulators or existing anticancer agents.

It is known that PD-1 is expressed in T cells or the like and is responsible for the immune checkpoint (Pharmacogenomics and Personalized Medicine, 2014; 7: 357-365, Current Opinion in Immunology, 2014; 27: 89-97). When PD-L1 and PD-L2, which are ligands of PD-1, are bound, activation of T cells is suppressed, and thereby immune response is hindered. For example, activated effector T cells recognize cancer cells and produce inflammatory cytokines such as interferon gamma. On the other hand, cancer cells react to the inflammatory cytokine and increase the expression of PD-L1, and thus suppress the immune response by PD-1-positive effector T cells. Thus, cancer cells have a function of escaping from the immunosurveillance against cancer by utilizing the PD-1/PD-L1 route. Therefore, the PD-1/PD-L1 route is considered to be one of the main molecular mechanisms of immunosuppression in the cancer microenvironment (Pharmacogenomics and Personalized Medicine, 2014; 7: 357-365, Current Opinion in Immunology, 2014; 27: 89-97).

As an antibody that inhibits the binding of PD-1 and PD-L1, nivolumab, which is an anti-PD-1 antibody, has been marketed as a therapeutic agent for malignant melanoma and non-small cell lung cancer, and pembrolizumab has been marketed as a therapeutic agent for malignant melanoma. Other several anti-PD-1 antibodies or anti-PD-L1 antibodies also have been under clinical development as a therapeutic agent for malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C. In double blind randomized phase 3 study Check Mate-066 in which nivolumab was used as a first-line drug against malignant melanoma, it was reported that overall survival in 72.9% of a nivolumab group was extended; however, the existence of patients who failed to respond was also recognized.

Regarding the immunotherapy, clinical trial result of combination therapy in which drugs having different mechanisms are combined, for example, clinical trial result of combination therapy of nivolumab, which is the anti-PD-1 antibody against malignant melanoma, and ipilimumab, which is an anti CTLA-4 antibody, has been reported (Pharmacogenomics and Personalized Medicine, 2014; 7: 357-365, Current Opinion in Immunology, 2014; 27: 89-97).

As the antibody that inhibits the binding of CTLA-4 and CD80 or CD86, ipilimumab, which is the anti CTLA-4 antibody, has been marketed as a therapeutic agent for malignant melanoma, and has been under clinical development as the therapeutic agent for non-small cell lung cancer, small cell lung cancer, prostate cancer, and the like.

Regarding an IDO inhibitor, INCB-024360 has been under clinical development as a therapeutic agent for malignant melanoma, fallopian tube cancer, ovarian cancer, peritoneal carcinoma up to now.

Dendritic cells present in blood and lymphatic tissues are known to activate T cells via inflammatory cytokines. It is reported that AXL, MER and TYRO3, which are subfamilies of receptor tyrosine kinases in dendritic cells, bond to type I IFN receptor (IFNAR) and induce suppressor of cytokine signaling 1 and 3 (SOCS 1/3) to inhibit Toll-like receptor 4 (TLR4) signal, and suppress the expression of inflammatory cytokines, and thereby the immune response is controlled to be negatively regulated. In addition, it is reported that the immune function is deteriorated by AXL (Cell. 2007 Dec. 14; 131(6): 1124-36.).

The AXL is a protein having a cellular transmembrane domain in the center, a tyrosine kinase domain on the carboxyl terminal side, and an extracellular domain on the amino terminal side. So far, overexpression of AXL has been reported in acute leukemia, astrocytoma, breast cancer, colon cancer, esophageal cancer, gastrointestinal stromal tumor, stomach cancer, hepatocellular carcinoma, Kaposi's sarcoma, lung cancer, melanoma, ovarian cancer, osteosarcoma, pancreatic duct adenocarcinoma, renal cell carcinoma, prostate cancer, thyroid cancer, and endometrial carcinoma (Mol. Cancer Ther. 2011 October; 10(10): 1763-73.).

The MER is a protein having a cellular transmembrane domain in the center, a tyrosine kinase domain on the carboxyl terminal side, and an extracellular domain on the amino terminal side. Overexpression of MER has been reported in acute leukemia, acute lymphocytic leukemia, glioma, osteosarcoma, prostate cancer, schwannoma, mantle cell lymphoma, and rhabdomyosarcoma cells (Nat Rev Cancer. 2014 December; 14(12): 769-85.).

In addition, it is reported that MER lowers immune function (J Clin Invest. 2013 Aug. 1; 123(8): 3231-42.). It is reported that MER inhibits the production of inflammatory cytokines such as IL-12 in dendritic cells and suppresses the activation of CD4 positive (for positive, it may be expressed as "+", and the negative may be expressed as "−") T cells and CD8+ T cells. It is reported that expression of IL-12, which is inflammatory cytokines, is induced by tumor transplantation in MER knockout mice compared to wild type mice, and tumor growth and metastasis are suppressed.

It is known that 6-ethyl-3-({3-methoxy-4-[4-(4-methyl-piperazin-1-yl)piperidin-1-yl]phenyl}amino)-5-(tetrahydro-2H-pyran-4-ylamino)pyrazine-2-carboxamide (hereinafter, referred to as "compound A" in some cases) or a pharmaceutically acceptable salt thereof has an inhibitory effect on various kinases including AXL, and inhibits the proliferation of tumor cells in which these kinases are involved, and thus is useful as an active ingredient of a pharmaceutical composition for treating cancer (Patent Documents 1 and 2).

RELATED ART

Patent Document

[Patent Document 1] WO 2010/128659
[Patent Document 2] WO 2015/119122

DISCLOSURE OF INVENTION

Problems to be Solved by the Invention

A compound useful as an active ingredient of a pharmaceutical composition, for example, a pharmaceutical composition for cancer immunotherapy, and/or a pharmaceutical composition for immunological activation is provided.

Means for Solving the Problem

The present inventors have conducted intensive studies for the purpose of creating a pharmaceutical composition for cancer immunotherapy and/or a pharmaceutical composition for immunological activation. As a result, the present inventors have found that a compound A, that is, 6-ethyl-3-({3-methoxy-4-[4-(4-methylpiperazin-1-yl)piperidin-1-yl]phenyl}amino)-5-(tetrahydro-2H-pyran-4-ylamino) pyrazine-2-carboxamide or a pharmaceutically acceptable salt thereof has an excellent immunological activation effect, and a pharmaceutical composition containing a compound A or a pharmaceutically acceptable salt thereof as an active ingredient is expected to be used as a pharmaceutical composition for cancer immunotherapy and/or as a pharmaceutical composition for immunological activation based on the above-described effect, thereby completing the present invention.

Thus, the present invention relates to a pharmaceutical composition for cancer immunotherapy comprising a compound A or a pharmaceutically acceptable salt thereof as an active ingredient, in one aspect, a pharmaceutical composition for cancer immunotherapy against cancer acquiring an immune escape mechanism due to expression of AXL and/or MER, comprising the compound A or the pharmaceutically acceptable salt thereof as an active ingredient, in one aspect, a pharmaceutical composition for immunological activation comprising the compound A or a pharmaceutically acceptable salt thereof as an active ingredient, in one aspect, a pharmaceutical composition for immunological activation against cancer acquiring an immune escape mechanism due to expression of AXL and/or MER, comprising the compound A or the pharmaceutically acceptable salt thereof as an active ingredient, and in one aspect, a pharmaceutical composition for immunological activation against cancer acquiring an immune escape mechanism due to expression of AXL and/or MER, mediated by an effect of increasing the number of CD8 positive cells, comprising the compound A or a pharmaceutically acceptable salt thereof.

An aspect of the present invention will be described below.

(1) A pharmaceutical composition for cancer immunotherapy comprising a compound A or a pharmaceutically acceptable salt thereof as an active ingredient. In one aspect, a pharmaceutical composition for cancer immunotherapy against cancer acquiring an immune escape mechanism due to expression of AXL and/or MER, comprising the compound A or the pharmaceutically acceptable salt thereof as an active ingredient. In one aspect, a pharmaceutical composition for immunological activation comprising the compound A or the pharmaceutically acceptable salt thereof as an active ingredient. In one aspect, the pharmaceutical composition for immunological activation against cancer acquiring an immune escape mechanism due to expression of AXL and/or MER, comprising the compound A or the pharmaceutically acceptable salt thereof an active ingredient. In one aspect, the pharmaceutical composition for immunological activation against cancer acquiring an immune escape mechanism due to expression of AXL and/or MER, mediated by an effect of increasing the number of CD8 positive cells comprising the compound A or the pharmaceutically acceptable salt thereof.

(2) Use of the compound A or the pharmaceutically acceptable salt thereof for the manufacture of a pharmaceutical composition for cancer immunotherapy. In one aspect, use of the compound A or the pharmaceutically acceptable salt thereof for the manufacture of a pharmaceutical composition for cancer immunotherapy against cancer acquiring an immune escape mechanism due to expression of AXL and/or MER. In one aspect, use of the compound A or the pharmaceutically acceptable salt thereof for the manufacture of a pharmaceutical composition for immunological activation. In one aspect, use of the compound A or the pharmaceutically acceptable salt thereof for the manufacture of a pharmaceutical composition for immunological activation against cancer acquiring an immune escape mechanism due to expression of AXL and/or MER. In one aspect, use of the compound A or the pharmaceutically acceptable salt thereof for the manufacture of a pharmaceutical composition for immunological activation against cancer acquiring an immune escape mechanism due to expression of AXL and/or MER, mediated by an effect of increasing the number of CD8 positive cells.

(3) Use of the compound A or the pharmaceutically acceptable salt thereof for cancer immunotherapy. In one aspect, use of the compound A or the pharmaceutically acceptable salt thereof for cancer immunotherapy against cancer acquiring the immune escape mechanism due to expression of AXL and/or MER. In one aspect, use of the compound A or the pharmaceutically acceptable salt thereof for immunological activation. In one aspect, use of the compound A or the pharmaceutically acceptable salt thereof for immunological activation against cancer acquiring an immune escape mechanism due to expression of AXL and/or MER. In one aspect, use of the compound A or the pharmaceutically acceptable salt thereof for immunological activation against cancer acquiring an immune escape mechanism due to expression of AXL and/or MER, mediated by an effect of increasing the number of CD8 positive cells.

(4) A compound A or a pharmaceutically acceptable salt thereof for cancer immunotherapy. In one aspect, the compound A or the pharmaceutically acceptable salt thereof for cancer immunotherapy against cancer acquiring the immune escape mechanism due to expression of AXL and/or MER. In one aspect, the compound A or the pharmaceutically acceptable salt thereof for immunological activation. In one aspect, the compound A or the pharmaceutically acceptable salt thereof for immunological activation against cancer acquiring an immune escape mechanism due to expression of AXL and/or MER. In one aspect, the compound A or the pharmaceutically acceptable salt thereof for immunological activation against cancer acquiring an immune escape mechanism due to expression of AXL and/or MER, mediated by an effect of increasing the number of CD8 positive cells.

(5) A method for treating cancer through anti-tumor immunity, comprising administering an effective dose of the compound A or the pharmaceutically acceptable salt thereof to a subject. In one aspect, a method for treating cancer through anti-tumor immunity against cancer acquiring an immune escape mechanism due to expression of AXL and/or MER, comprising administering an effective dose of the compound A or the pharmaceutically acceptable salt thereof to a subject. In one aspect, a method for treating cancer through immunological activation, comprising administering an effective dose of the compound A or the pharmaceutically acceptable salt thereof to a subject. In one aspect, a method for treating cancer through an immunological activation against cancer acquiring an immune escape mechanism due to expression of AXL and/or MER, comprising administering an effective dose of the compound A or the pharmaceutically acceptable salt thereof to a subject. In one aspect, a method for treating cancer through an immunological activation against cancer acquiring an immune escape mechanism due to expression of AXL and/or MER, mediated by an effect of increasing the number of CD8 positive cells, comprising administering an effective dose of the compound A or the pharmaceutically acceptable salt thereof to a subject.

(6) The pharmaceutical composition according to (1) wherein the pharmaceutical composition is administered in combination with a monoclonal antibody inhibiting binding of PD-1 and PD-L1.

(7) The pharmaceutical composition according to (6) wherein the monoclonal antibody inhibiting the binding of PD-1 and PD-L1 is selected from nivolumab, pembrolizumab, atezolizumab, pidilizumab, avelumab, and durvalumab.

(8) The pharmaceutical composition according to (7) wherein the pharmaceutical composition is administered simultaneously, separately, continuously, or intermittently with the monoclonal antibody inhibiting the binding of PD-1 and PD-L1.

(9) The pharmaceutical composition according to any one of (6) to (8) for combination therapy with the monoclonal antibody inhibiting the binding of PD-1 and PD-L1.

(10) A pharmaceutical composition according to (1), and (6) to (9) for treatment of malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C.

(11) The pharmaceutical composition according to any one of (1) and (6) to (10) comprising the compound A or the pharmaceutically acceptable salt thereof and a pharmaceutically acceptable excipient.

(12) The pharmaceutical composition according to any one of (1) and (6) to (11), wherein the compound A or the pharmaceutically acceptable salt thereof is hemifumarate of the compound A.

(13) The use according to (2) wherein the compound A or the pharmaceutically acceptable salt thereof is hemifumarate of the compound A.

(14) The use according to (3) wherein the compound A or the pharmaceutically acceptable salt thereof is hemifumarate of the compound A.

(15) In (4), the compound A or the pharmaceutically acceptable salt thereof according to (4) wherein the compound A or the pharmaceutically acceptable salt thereof is hemifumarate of the compound A.

(16) The therapeutic method according to (5) wherein the compound A or the pharmaceutically acceptable salt thereof is hemifumarate of the compound A.

The present invention also relates to the following inventions.

(17) The use according to (2) or (13) wherein the pharmaceutical composition is administered in combination with a monoclonal antibody inhibiting binding of PD-1 and PD-L1.

(18) The use according to (17) wherein the monoclonal antibody inhibiting the binding of PD-1 and PD-L1 is an antibody selected from nivolumab, pembrolizumab, atezolizumab, pidilizumab, avelumab, and durvalumab.

(19) The use according to (17) or (18) wherein the pharmaceutical composition is administered simultaneously, separately, continuously, or intermittently with the monoclonal antibody inhibiting the binding of PD-1 and PD-L1.

(20) The use according to (17) to (19) for cancer treatment for a subject receiving the monoclonal antibody inhibiting the binding of PD-1 and PD-L1.

(21) The use according to (17) to (20) for treatment of malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C.

The present invention also relates to the following inventions.

(22) The use according to (3) or (14) wherein the compound A or the pharmaceutically acceptable salt thereof is administered in combination with a monoclonal antibody inhibiting binding of PD-1 and PD-L1.

(23) The use according to (22) wherein the monoclonal antibody inhibiting the binding of PD-1 and PD-L1 is the antibody selected from nivolumab, pembrolizumab, atezolizumab, pidilizumab, avelumab, and durvalumab.

(24) The use according to (22) or (23) wherein the compound A or the pharmaceutically acceptable salt thereof is administered simultaneously, separately, continuously, or intermittently with the monoclonal antibody inhibiting the binding of PD-1 and PD-L1.

(25) The use according to (22) to (24) for cancer treatment for a subject receiving the monoclonal antibody inhibiting the binding of PD-1 and PD-L1.

(26) The use according to (22) to (25) for treatment of malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C.

The present invention also relates to the following inventions.

(27) The compound or the salt thereof according to (4) or (15), which is administered in combination with a monoclonal antibody inhibiting binding of PD-1 and PD-L1.

(28) The compound or the salt thereof according to (27) wherein the monoclonal antibody inhibiting the binding of PD-1 and PD-L1 is an antibody selected from nivolumab, pembrolizumab, atezolizumab, pidilizumab, avelumab, and durvalumab.

(29) The compound or the salt thereof according to (27) or (28), which is administered simultaneously, separately, continuously, or intermittently with the monoclonal antibody inhibiting the binding of PD-1 and PD-L1.

(30) The compound or the salt thereof according to (27) to (29) for cancer treatment for a subject receiving the monoclonal antibody inhibiting the binding of PD-1 and PD-L1.

(31) The compound or the salt thereof according to (27) to (30) for treatment of malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C.

The present invention also relates to the following inventions.

(32) A method for cancer immunotherapy comprising administering a therapeutically effective dose of the monoclonal antibody inhibiting binding of PD-1 and PD-L1 for combination therapy, and a therapeutically effective dose of the compound A or the pharmaceutically acceptable salt thereof for combination therapy, in combination.

(33) The therapeutic method according to (32) wherein the compound A or the pharmaceutically acceptable salt thereof is hemifumarate of the compound A.

(34) The therapeutic method according to (32) or (33) wherein the monoclonal antibody inhibiting the binding of PD-1 and PD-L1 is an antibody selected from nivolumab, pembrolizumab, atezolizumab, pidilizumab, avelumab, and durvalumab.

(35) The therapeutic method according to (32) to (34) wherein the compound A or the pharmaceutically acceptable salt thereof is simultaneously, separately, continuously, or intermittently administered with the monoclonal antibody inhibiting the binding of PD-1 and PD-L1.

(36) The therapeutic method according to (32) to (35) for cancer treatment for a subject receiving the monoclonal antibody inhibiting the binding of PD-1 and PD-L1.

(37) The therapeutic method according to (32) to (36) for treatment of malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C.

The present invention also relates to the following inventions.

(38) An agent for treating cancer by immune activation, comprising the compound A or the pharmaceutically acceptable salt thereof.

(39) The agent according to (38), which is used in combination with the monoclonal antibody inhibiting the binding of PD-1 and PD-L1.

(40) The agent according to (39) in which the monoclonal antibody inhibiting the binding of PD-1 and PD-L1 is an antibody selected from nivolumab, pembrolizumab, atezolizumab, pidilizumab, avelumab, and durvalumab

(41) The agent according to (39) or (40) wherein the agent is simultaneously, separately, continuously, or intermittently with the monoclonal antibody inhibiting the binding of PD-1 and PD-L1.

(42) The agent according (39) to (41) for cancer treatment for a subject receiving the monoclonal antibody inhibiting the binding of PD-1 and PD-L1.

(43) The agent of (39) to (42) for treatment of malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, or chronic hepatitis C.

Note that, "subject" is a human or other animals in need of prevention or treatment thereof, and in one aspect, the subject is a human in need of prevention or treatment thereof.

Effects of the Invention

The compound A or a pharmaceutically acceptable salt thereof which is an active ingredient of a pharmaceutical composition according to the present invention has an immunological activation effect, and is expected to be used as a cancer immunotherapy agent and/or as an immunological activation agent based on the above-described effect.

EMBODIMENTS FOR CARRYING OUT THE INVENTION

Figure 1:
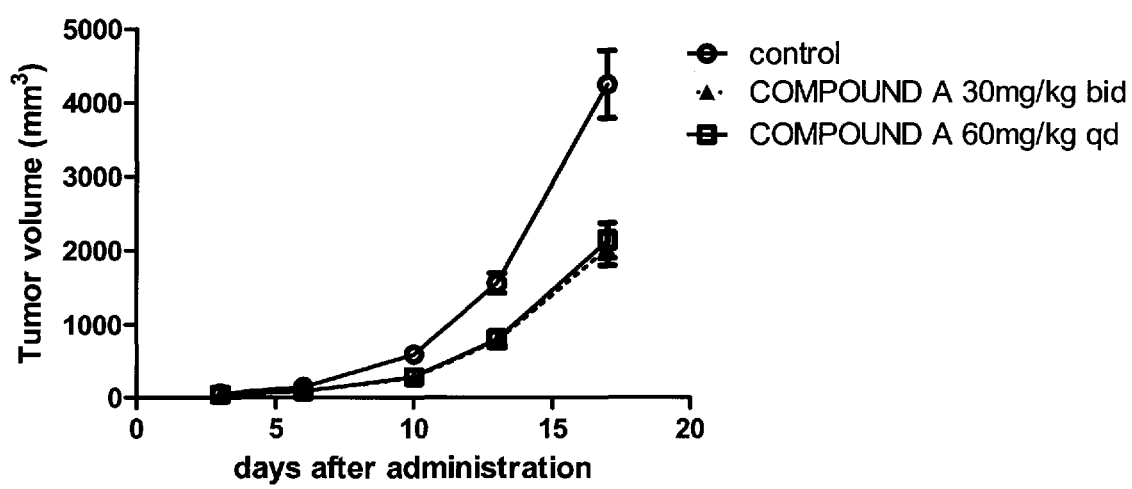
FIG. 1 is a diagram illustrating a tumor volume of a group in which a compound A (COMPOUND A) was administered to MC38 subcutaneous cancer-bearing mice described in Example 1. COMPOUND A 30 mg/kg bid represents a group in which hemifumarate of the compound A was orally administered at a dose of 30 mg/kg (in terms of free form) twice a day for 17 days, COMPOUND A 60 mg/kg qd represents a group in which hemifumarate of the compound A was orally administered at a dose of 60 mg/kg (in terms of free form) once a day for 17 days, and control represents a control group in which the compound A was not administered. Further, a vertical axis represents the tumor volume ($mm^3$), and a horizontal axis represents days after administration.

Hereinafter, the present invention will be described in detail.

As described above, the chemical name of compound A is 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide, and the chemical structure of which is as illustrated below.

[Chem. 1]

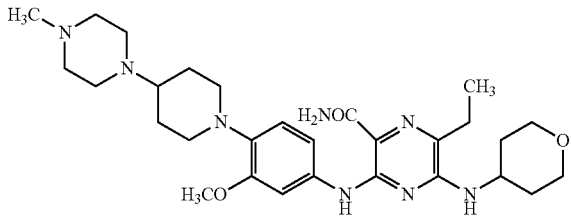

In many cancers, there is a part called "stroma" in addition to cancer cells, and the cancer microenvironment means a portion of the stroma, where cells called fibroblasts, as well as blood vessels, lymph vessels and connective tissue present among these cells are present and form a distinctive structure.

The immune checkpoint means a body check mechanism that suppresses an excessive action of an immune response.

The cancer immunotherapy means re-activating immune cells, particularly, activated T cells, whose ability to inhibit cancer cell proliferation or to reduce or eliminate cancer cells (hereinafter, referred to as antitumor activity) is deteriorated, and/or increasing the number of immune cells, particularly, the activated T cells so as to perform an anticancer treatment.

The treatment of cancer through the cancer immunity means a treatment of cancer with immunity in the body, particularly, a treatment of cancer with activated T cells.

The immune activation means re-activating immune cells, particularly, activated T cells, whose ability to inhibit cancer cell proliferation or to reduce or eliminate cancer cells (hereinafter, referred to as antitumor activity) is deteriorated, and/or increasing the number of immune cells, particularly, the activated T cells.

The cancer acquiring the immune escape mechanism due to expression of AXL and/or MER means cancer acquiring an immune escape mechanism as a result of deterioration of the ability to inhibit the proliferation of cancer cells or reduce or eliminate cancer cells by the immune cells, particularly, the activated T cells, due to overexpression of AXL and/or MER in the immune cells as compared to the normal issues. The cancer to which the present invention is applicable is not particularly limited, and examples thereof include malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, chronic hepatitis C, colon cancer, breast cancer, fallopian tube cancer, ovarian cancer, and peritoneal cancer. In one aspect, examples thereof include malignant melanoma, non-small cell lung cancer, renal cell carcinoma, recurrent glioblastoma, head and neck cancer, stomach cancer, esophageal cancer, colorectal cancer, bladder cancer, urothelial carcinoma, hepatocellular carcinoma, prostate cancer, Merkel cell carcinoma, non-Hodgkin's lymphoma, Hodgkin lymphoma, B cell lymphoma, acute myeloid leukemia, and chronic hepatitis C. In one aspect, examples thereof include non-small cell lung cancer, colon cancer, and breast cancer. In one aspect, examples thereof include non-small cell lung cancer, and acute myeloid leukemia.

In one aspect, the pharmaceutical composition according to the present invention is administered in combination with a monoclonal antibody inhibiting the binding of PD-1 and PD-L1, and examples of the monoclonal antibody inhibiting the binding of PD-1 and PD-L1 include an antibody selected from nivolumab, pembrolizumab, atezolizumab, pidilizumab, avelumab, and durvalumab.

In addition, the pharmaceutical composition of the present invention may be simultaneously, separately, continuously, or intermittently administered with the monoclonal antibody inhibiting the binding of PD-1 and PD-L1.

In one aspect, the pharmaceutical composition according to the present invention is administered in combination with monoclonal antibody inhibiting the binding of PD-1 and PD-L1, and the combination effect is expected to be exerted on cancer in which the monoclonal antibody inhibiting the binding of PD-1 and PD-L1 is effective. The cancer to which the monoclonal antibody inhibiting the binding of PD-1 and PD-L1 is effective includes, for example, solid cancer. Examples of such solid cancer include malignant melanoma (for example, metastatic malignant melanoma), kidney cancer (for example, renal cell carcinoma, clear cell carcinoma), prostate cancer (for example, hormone refractory prostate adenocarcinoma), breast cancer, lung cancer (for example, non-small cell lung cancer), pancreatic cancer, colorectal cancer, hepatocellular carcinoma, biliary tract cancer, stomach cancer, ovarian cancer, esophageal cancer, urothelial carcinoma, colon cancer, bone cancer, skin cancer, head and neck cancer, skin or orbital malignant melanoma, uterine cancer, rectal cancer, anal cancer, testicular cancer, uterine cancer, fallopian tube carcinoma, endometrial carcinoma, cervical carcinoma, vaginal carcinoma, vulvar carcinoma, small intestine cancer, endocrine system cancer, thyroid cancer, parathyroid cancer, adrenal cancer, soft tissue sarcoma, urethral cancer, penile cancer, childhood solid cancer, bladder cancer, cancer of kidney or ureter, pelvic carcinoma, central nervous system (CNS) tumor, tumor angiogenesis, spinal tumor, brain stem glioma, pituitary adenoma, Kaposi's sarcoma, squamous cell carcinoma, epidermoid cancer, environment-induced cancer including asbestos-induced cancer, and the combination thereof. Examples of the solid cancer in which the pharmaceutical composition can be more expected to be applied include malignant melanoma (for example, metastatic malignant melanoma), kidney cancer (for example, renal cell carcinoma and clear cell carcinoma), prostate cancer (for example, hormone refractory prostate adenocarcinoma), breast cancer, lung cancer (for example, non-small cell lung cancer), pancreatic cancer, colorectal cancer, hepatocellular carcinoma, biliary tract cancer, stomach cancer, ovarian cancer, esophageal cancer, urothelial carcinoma, and the combination thereof, and examples of the solid cancer in which the pharmaceutical composition can be still more expected to be applied include malignant melanoma (for example, metastatic malignant melanoma), kidney cancer (for example, renal cell carcinoma, clear cell carcinoma), prostate cancer, lung cancer (for example, non-small cell lung cancer), colorectal cancer, hepatocellular carcinoma, biliary tract cancer, and the combination thereof.

The pharmaceutical composition can be expected to be effective not only for patients with solid cancer but also for patients with blood cancer. Examples of the blood cancer include follicular lymphoma, chronic lymphocytic leukemia, small lymphocytic lymphoma, multiple myeloma, mantle cell lymphoma, diffuse large B cell lymphoma, B cell prolymphocytic leukemia, acute lymphocytic leukemia, histiocytic lymphoma, acute myeloid leukemia, acute megakaryoblastic leukemia, undifferentiated large cell lymphoma, acute T cell lymphoma, lymphoblastic leukemia, chronic myelogenous leukemia, and the combination thereof.

The compound A or the pharmaceutically acceptable salt thereof can be obtained according to the method disclosed in Patent Document 1 (WO 2010/128659) or by a modified method thereof.

In addition, "the pharmaceutically acceptable salt of the compound A" means the acid addition salt of the compound A, and specifically, acid addition salt with inorganic acid such as hydrochloric acid, hydrobromic acid, hydriodic acid, sulfuric acid, nitric acid, phosphoric acid; and organic acid such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid.

Note that, in one aspect, examples of "the pharmaceutically acceptable salt of the compound A" include a compound A, in one aspect, an acid addition salt of the compound A with fumaric acid, and, in one aspect, hemifumarate of the compound A.

Examples of the active ingredient of the pharmaceutical composition according to the present invention may be a solvate of the compound A, specifically, for example, a hydrate or an ethanol solvate, and further may be a solvate of an acid addition salt of the compound A.

The pharmaceutical composition containing the compound A or the pharmaceutically acceptable salt thereof can be prepared by using an excipient commonly used in this field, that is, an excipient for pharmaceuticals and a carrier for pharmaceuticals through the commonly used methods.

The administration may be any of oral administration with tablets, pills, capsules, granules, powders, solutions, and the like, and parenteral administration with injections such as intra-articular, intravenous, intramuscular, and the like, suppositories, transdermal solutions, ointments, transdermal patches, transmucosal solutions, transmucosal patches, and inhalant.

As the solid composition for oral administration, tablets, powders, granules and the like are used. In such a solid composition, one or more active ingredients are mixed with at least one inert excipient. The composition may contain an inert additive such as a lubricant, a disintegrant, a stabilizer, and a solubilizing agent according to the conventional method. The tablets or pills may be coated with a sugar coating or a film of a substance which can be dissolved in a stomach or small intestine, if necessary.

The liquid composition for the oral administration includes a pharmaceutically acceptable emulsion, a solution, a suspension, syrup, an elixir, and the like, and further includes commonly used inert diluent such as purified water or ethanol. The liquid composition may include an adjuvant such as a solubilizing agent, a wetting agent, and a suspending agent, a sweetening agent, a flavor, an aromatic, and a preservative, in addition to the inert diluent.

The injection for parenteral administration includes a sterile aqueous or nonaqueous solution, a suspension, or an emulsion. Examples of the aqueous solvent include distilled water for injection or physiological saline. Examples of the nonaqueous solvent include alcohols such as ethanol. Such a composition may further include an isotonizing agent, a preservative, a wetting agent, an emulsifying agent, a dispersing agent, a stabilizing agent, or a solubilizing agent. For example, these compositions are sterilized by filtration through a bacteria-retaining filter, blending of a sterilizing agent, or irradiation. In addition, these compositions can be used for preparing a sterile solid composition, and the sterile solid composition can be used after dissolved or suspended in sterile water or a sterile injectable solvent.

In general, for oral administration, the daily dose is about 0.001 mg/kg to 100 mg/kg, preferably 0.01 mg/kg to 30 mg/kg, and more preferably 0.1 to 10 mg/kg, per body weight, administered in one portion or in 2 to 4 separate portions. In the case of intravenous administration, the daily dose is suitably administered from about 0.0001 mg/kg to 10 mg/kg per body weight, once a day or two or more times a day. In addition, a transmucosal agent is administered at a dose from about 0.001 mg/kg to 100 mg/kg per body weight, once a day or two or more times a day. Doses are determined as appropriate according to the individual according to the symptoms, age, gender, and the like.

Although varying depending on administration routes, formulations, administration sites, or the types of excipients or additives, the pharmaceutical composition of the present invention contains 0.01% by weight to 99% by weight, and in one aspect, 0.01% by weight to 50% by weight of the compound A or a pharmaceutically acceptable salt thereof as an active ingredient.

The pharmaceutical composition according to the present invention can be used in combination with various therapeutic agents. The combination may be administered simultaneously, or separately in succession, or at a desired time interval. For co-administration, it may be a compounding agent or separately formulated. Examples of drugs that can be particularly used in combination include a platinum preparation such as cisplatin, carboplatin, antimetabolite such as gemcitabine, pemetrexed, 5-fluorouracil, capecitabine, and bendamustine, a microtubule polymerization inhibitor such as paclitaxel and vinorelbine, an angiogenesis inhibitors such as bevacizumab, a topoisomerase inhibitor such as irinotecan and etoposide, a cytokine preparation such as interferon, a kinase inhibitor such as sunitinib, pazopanib, sorafenib, and axitinib, antiandrogen such as enzartamide, and an alkylating agent such as temozolomide, dacarbazine, cyclophosphamide, and ifosfamide.

EXAMPLES

Pharmacological effects of the pharmaceutical composition according to the present invention were confirmed by the following examples.

Example 1

Evaluation of Anti-Tumor (In Vivo) of Compound a with Respect to Colon Carcinoma Cell Line MC38 Cancer-Bearing Model The colon cancer cell line MC38 cells (National Cancer Institute) were cultured in Dulbecco's modified Eagle's minimum essential medium (DMEM) supplemented with 10% Fetal Bovine Serum (FBS). MC38 subcutaneous cancer-bearing mice were subsequently prepared by subcutaneously transplanting MC38 cells on the back of C57BL/6J mice (female, Charles river, Japan). After confirming the engraftment of the tumor, the change in the tumor volume of each of the group (COMPOUND A 30 mg/kg bid) in which hemifumarate of the compound A, which is a test compound, dissolved in 0.5% of methyl cellulose is orally administered at a dose of 30 mg/kg (in terms of free form) twice a day for 17 days, the group (COMPOUND A 60 mg/kg qd) in which hemifumarate of the compound A is orally administered at a dose of 60 mg/kg (in terms of free form) once a day for 17 days, and the control group in which the compound A is not administered, was measured at a frequency of twice a week.

The results are shown in FIG. 1. The group in which the test compound was administered (COMPOUND A 30 mg/kg bid and COMPOUND A 60 mg/kg qd) exhibited a strong effect of suppressing the increase in the tumor volume as compared with the control group.

From the above, it was confirmed that the compound A exhibited an anti-tumor effect in a syngeneic model in which colon carcinoma cell line MC38 was transplanted into C57BL/6J mouse having a normal immune function.

Example 2

Evaluation of Immune Activation of Compound a with Respect to Colon Carcinoma Cell Line MC38 Cancer-Bearing Model MC38 subcutaneous cancer-bearing mice were prepared by subcutaneously transplanting MC38 cells on the back of C57BL/6J mouse (female, Charles river, Japan). After confirming the engraftment of the tumor, hemifumarate of the compound A, which is the test compound, was orally administered to seven mice at a dose of 100 mg/kg (in terms of free form) once a day for seven days. As a control, 0.5% of methylcellulose was also orally administered to seven mice at the same dose of 100 mg/kg once a day for seven days, which was the same administration as the group administered at a 100 mg/kg. After measuring the tumor volume change on the 4th and 7th days, spleens and tumors were collected from a total of six mice of three examples (control-1, control-2, and control-3) extracted from the control group and three examples extracted from the compound A administered groups (COMPOUND A 100 mg/kg qd-1, COMPOUND A 100 mg/kg qd-2, and COMPOUND A 100 mg/kg qd-3). Then, staining was performed with anti CD3 antibody (eBioscience), anti CD4 antibody (Biolegend), anti CD8 antibody (eBioscienec), anti CD45 antibody (Biolegend), and the number of positive cells of each antigen was measured using a flow cytometer (BD FACS Verse).

Figure 2:
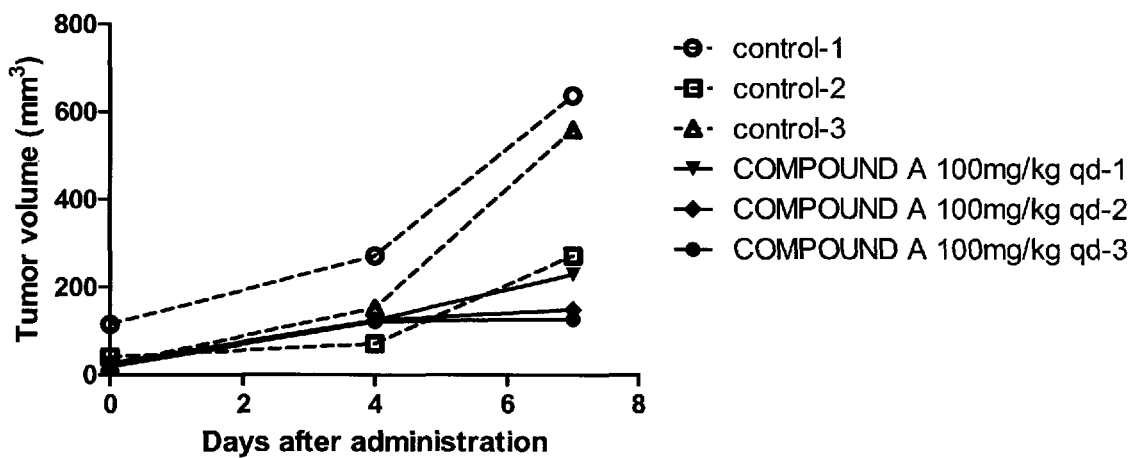
FIG. 2 is a diagram illustrating tumor volumes of individuals in which the compound A (COMPOUND A) was administered to the MC38 subcutaneous cancer-bearing mice described in Example 2. COMPOUND A 100 mg/kg qd-1, COMPOUND A 100 mg/kg qd-2, and COMPOUND A 100 mg/kg qd-3 represent three examples (COMPOUND A 100 mg/kg qd) in which hemifumarate of the compound A was orally administered at a dose of 100 mg/kg (in terms of free form) one a day for seven days, and which was extracted from the compound A administered group. In addition, control-1, control-2, and control-3 represent three control example in which 0.5% of methyl cellulose was orally administered in the same administration as that of the compound A (COMPOUND A) one a day for seven days, and which was extracted from the control groups. Further, a vertical axis represents the tumor volume ($mm^3$), and a horizontal axis represents days after administration.

The results of the change in tumor volume are shown in FIG. 2. In control groups (control-1, control-2, and control-3), an increase in the tumor volume was observed over time; whereas in COMPOUND A 100 mg/kg qd-2 and COMPOUND A 100 mg/kg qd-3 which are compound A administered groups, the increase in the tumor volume was hardly observed.

Figure 3:
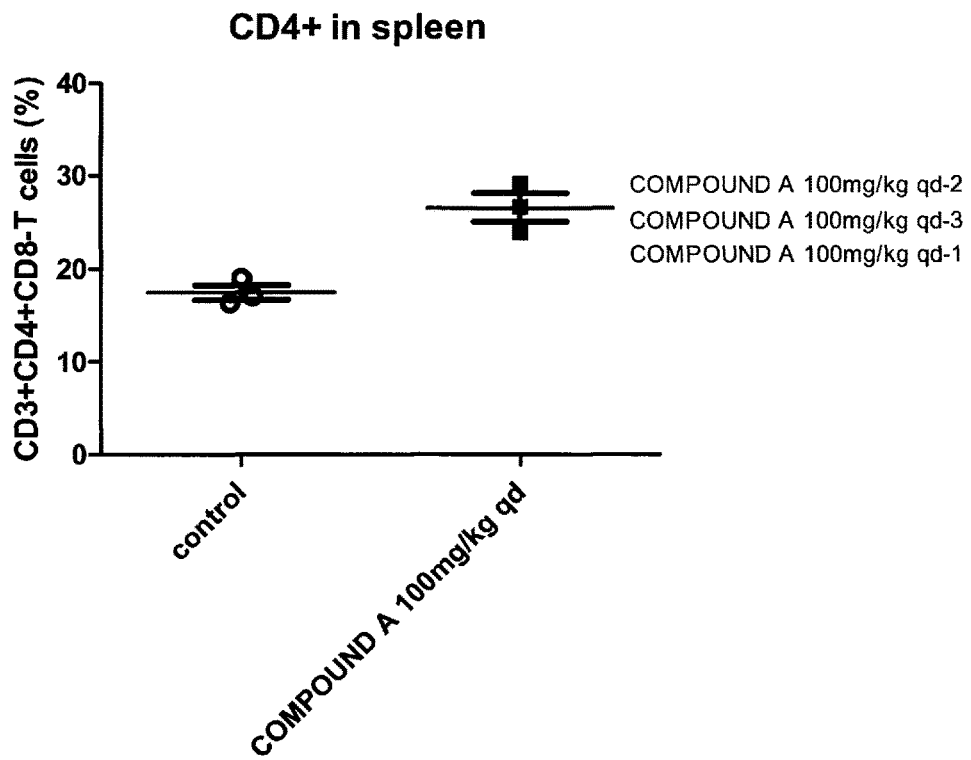
FIG. 3 is a result of analyzing CD4+ T cells (CD4+ in spleen) in spleen of the group in which the compound A (COMPOUND A) was administered to the MC38 subcutaneous cancer-bearing mouse described in Example 2. The vertical axis represents the proportion of the number of cells of CD3+, CD4+, and CD8− (CD3+CD4+CD8− T cells (%)), that is, the proportion (%) of CD4+, and the horizontal axis represents the administered compounds (COMPOUND A 100 mg/kg qd, and control) described in FIG. 2.
Figure 4:
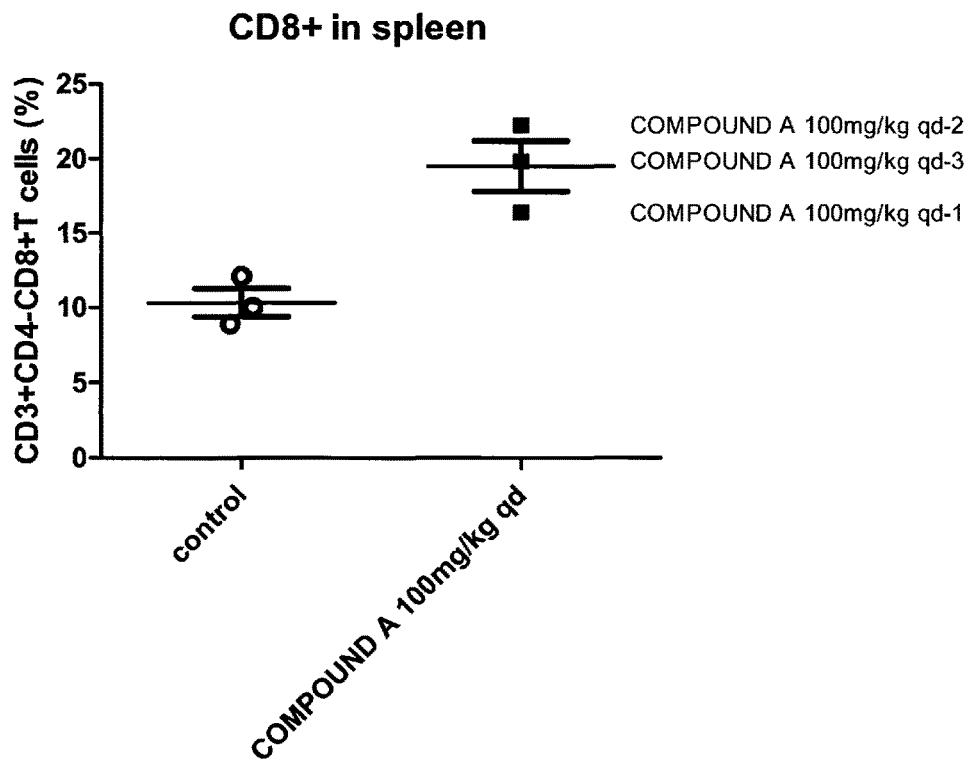
FIG. 4 is a result of analyzing CD8+ T cells (CD8+ in spleen) in spleen of the group in which the compound A (COMPOUND A) was administered to the MC38 subcutaneous cancer-bearing mouse described in Example 2. The vertical axis represents the proportion of the number of cells of CD3+, CD4−, and CD8+ (CD3+CD4−CD8+ T cells (%)), that is, the proportion (%) of CD8+, and the horizontal axis represents the administered compounds (COMPOUND A 100 mg/kg qd, and control) described in FIG. 2.

The proportion of the number of CD4+ cells in CD45+ and CD3+ cells in spleen is shown in FIG. 3, and the proportion of the number of CD8+ cells in CD45+ and CD3+ cells in spleen is shown in FIG. 4. As compared with the control groups, in the compound A administered mouse groups (COMPOUND A 100 mg/kg qd-1, COMPOUND A 100 mg/kg qd-2, and COMPOUND A 100 mg/kg qd-3), the increase in the number of CD4+ cells and CD8+ cells in spleen was observed.

Figure 5:
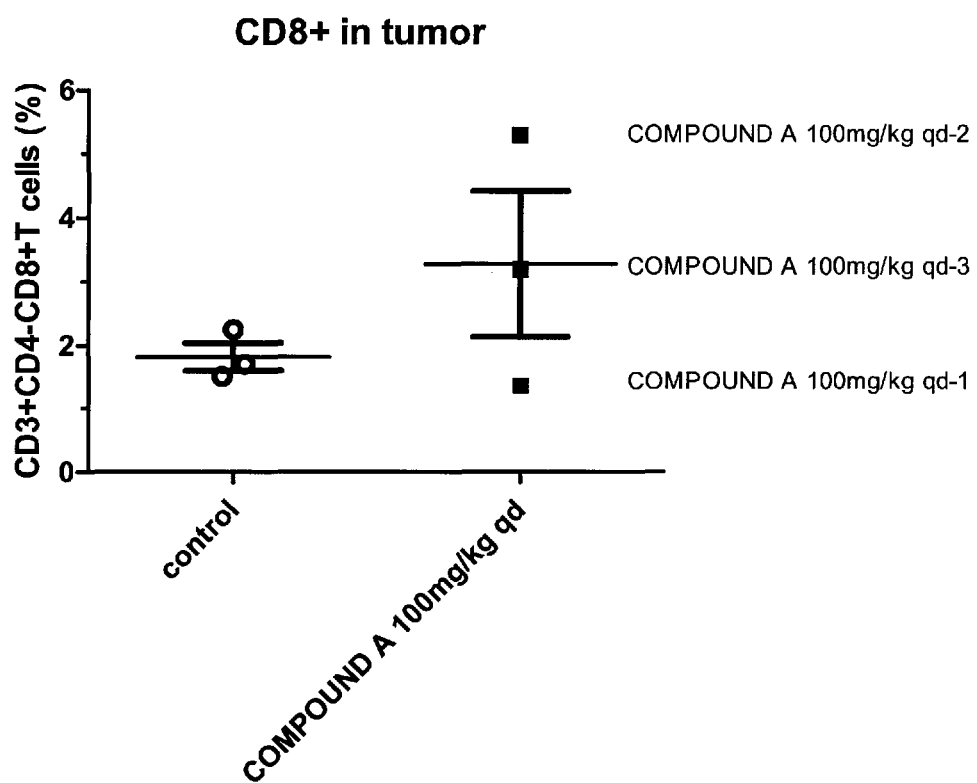
FIG. 5 is a result of analyzing CD8+ T cells (CD8+ in tumor) in tumor of the group in which the compound A (COMPOUND A) was administered to the MC38 subcutaneous cancer-bearing mouse described in Example 2. The vertical axis represents the proportion of the number of cells of CD3+, CD4−, and CD8+ (CD3+CD4−CD8+ T cells (%)), that is, the proportion (%) of CD8+, and the horizontal axis represents the administered compounds (COMPOUND A 100 mg/kg qd, and control) described in FIG. 2.

The proportion of the number of CD8+ cells in CD45+ and CD3+ cells in a tumor is shown in FIG. 5. Regarding the number of CD8+ cells in the tumor, in individuals (COMPOUND A 100 mg/kg qd-2, and COMPOUND A 100 mg/kg qd-3) in which the tumor growth was suppressed due to the administration of the compound A, the increase of the number of CD8+ cells was observed.

As described above, it was shown that the compound A promoted the increase in CD4 positive cells and CD8 positive cells, activated the immune function, and suppressed the tumor growth in individuals in which the immune function was activated. Based on this result, the compound A or the pharmaceutically acceptable salt thereof is expected to be used as an active ingredient of the pharmaceutical composition for treatment of cancer obtaining the immune escape mechanism due to the expression of AXL and/or MER.

Example 3

Anti-Tumor Evaluation on Syngeneic and Cancer-Bearing Mouse Model in Combination with PD-1/PD-L1 Antibody The effects of the combination of hemifumarate of the compound A and the anti-PD-1 antibody, which is a test compound according to the present invention, or the combination of hemifumarate of the compound A and the anti-PD-L1 antibody, which is a test compound according to the present invention, can be confirmed by evaluating the anti-tumor effect and the prolongation effect when the above compound is administered to the syngeneic and cancer-bearing mouse model. Examples of mouse tumor-derived cells include CT26, A20, J558, 4T1, and MC38.

INDUSTRIAL APPLICABILITY

The compound A or a pharmaceutically acceptable salt thereof, which is an active ingredient of a pharmaceutical composition according to the present invention, has an excellent immunological activation effect, and a pharmaceutical composition comprising the compound A or a pharmaceutically acceptable salt thereof as an active ingredient is expected to be used as a cancer immunotherapy agent and/or as an immunological activation agent based on the above-described effect.

The invention claimed is:

1. A method for immunological activation, comprising administering, to a subject in need thereof, a therapeutically effective amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof in combination with a monoclonal antibody inhibiting binding of PD-1 and PD-L1,
wherein said monoclonal antibody inhibiting the binding of PD-1 and PD-L1 is selected from the group consisting of nivolumab, pembrolizumab, atezolizumab, pidilizumab, avelumab, and durvalumab.

2. The method according to claim 1, wherein said 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof is administered simultaneously, separately, continuously, or intermittently with said monoclonal antibody inhibiting the binding of PD-1 and PD-L1.

3. The method according to claim 1, comprising administering 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate.

4. The method according to claim 2, comprising administering 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate.

* * * * *